United States Patent [19]

Ikari et al.

[11] 4,398,942
[45] Aug. 16, 1983

[54] HERBICIDALLY-ACTIVE PHENYLACETONITRILES

[75] Inventors: Hirotake Ikari, Urawa; Kanichi Kakizaki, Kazo, both of Japan

[73] Assignee: Rohm and Haas Company, Philadelphia, Pa.

[21] Appl. No.: 218,326

[22] Filed: Dec. 22, 1980

[51] Int. Cl.$^3$ .................. A01N 43/54; A01N 43/64; A01N 43/60; A01N 43/40
[52] U.S. Cl. .................................. 71/92; 71/66; 71/94
[58] Field of Search ................ 71/92, 94, 66

[56] References Cited

U.S. PATENT DOCUMENTS

| | | | |
|---|---|---|---|
| 3,821,394 | 6/1974 | Timmler et al. | 424/273 |
| 3,870,726 | 3/1975 | Jager et al. | 424/273 X |
| 3,897,438 | 7/1974 | Draber et al. | 71/92 X |
| 4,005,083 | 1/1977 | Buchel et al. | 424/245 |
| 4,009,021 | 2/1977 | Yib et al. | 71/92 |
| 4,167,576 | 9/1979 | Miller et al. | 424/273 R |

FOREIGN PATENT DOCUMENTS 754506  8/1971  Belgium.
867245 11/1978  Belgium.

OTHER PUBLICATIONS

Derwent Abstract 19614T/12, concerning BE 772402.

Primary Examiner—Catherine L. Mills
Attorney, Agent, or Firm—Lester E. Johnson

[57] ABSTRACT

There is disclosed a method for selectively regulating weed plant growth in transplanted rice fields under aquatic conditions which comprises applying to said weed plants an effective amount of a compound of the formula:

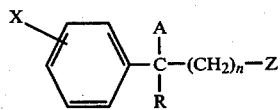

wherein:
X is selected from hydrogen, ($C_1$–$C_4$) alkyl, F, Cl, Br, $NO_2$, or $SO_2C_6H_5$;
R is selected from $C_6H_5$, $C_6H_4X$ wherein X is as defined above, straight or branched chain ($C_1$–$C_8$) alkyl, ($C_3$–$C_6$) saturated or unsaturated cycloaliphatic groups, $C_6H_5CH_2$ and $C_6H_5S$;
n is selected from O and the integers 1 and 2;
A is selected from CH or C≡CH; and
Z is a N-heterocyclic group;

or an agronomically acceptable acid addition salt thereof.

10 Claims, No Drawings

HERBICIDALLY-ACTIVE PHENYLACETONITRILES

BACKGROUND OF THE INVENTION

1. Field of the Invention

This invention relates to the use of certain N-heterocyclic ring-substituted phenylacetonitrile derivatives as herbicides which are effective against a variety of weeds, particularly barnyardgrass (*Echinochloa crusgalli*), as post-emergence and especially pre-emergence growth inhibitors in rice fields for transplanted rice under aquatic, or flood, conditions as occurs in rice paddys.

2. Description of the Prior Art

Buchel et al., U.S. Pat. No. 3,732,242, issued May 8, 1973, discloses phenylimidazolyl-fatty acid derivatives having the formula:

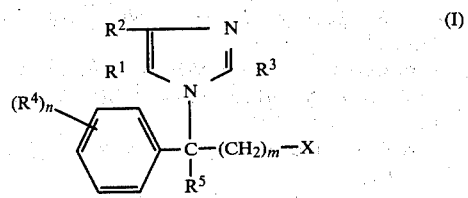

wherein:
- $R^1$, $R^2$ and $R^3$ are the same or different and are hydrogen or lower alkyl;
- $R^4$ is hydrogen, alkyl, lower alkoxy, lower alkyl mercapto, or an electronegative moiety;
- $R^5$ is benzene, benzene substituted by alkyl, lower alkoxy, lower alkylmercapto or an electronegative moiety, or $R^5$ is an aliphatic moiety;
- X is a carboxyl moiety or a grouping of a functional carboxylic acid derivative;
- m is 0, 1, 2, 3, 4, 5, or 6; and
- n is 0, 1 or 2, and pharmaceutically acceptable non-toxic salts thereof, and processes for the production of such compounds of the formula shown above. These compounds are particularly useful for their antimycotic activity and are intended to be administered to humans and animals.

A preferred group of compounds disclosed in this patent and represented by the formula (I) in the foregoing paragraph is that wherein X is a carboxyl group of the formula —COOR$^6$ wherein R$^6$ is straight or branched chain alkyl of 1 to 10 carbon atoms or benzyl or an amide group of the formula:

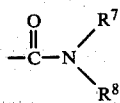

wherein R$^7$ and R$^8$ are the same or different, and are hydrogen or methyl, or R$^7$ and R$^8$ together with the amide nitrogen form a morpholino or piperidino ring. The salts may be formed with any of the known physiologically compatible acids such as hydrohalic acids, phosphorous acids, mono- and bifunctional carboxylic acids and hydroxycarboxylic acids.

Example 9 of this patent discloses the preparation of the specific compound, diphenyl-imidazolyl-acetonitrile, having the formula:

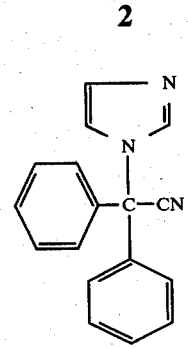

Buchel et al., U.S. Pat. No. 3,826,836 issued July 30, 1974, which is a division of the aforementioned U.S. Pat. No. 3,732,242, contains claims drawn to the pharmaceutical composition and the method of combatting mycotic infections disclosed in the earlier U.S. Pat. No. 3,732,242.

Buchel et al., U.S. Pat. No. 3,842,078 issued Oct. 15, 1974, which is also a division of U.S. Pat. No. 3,732,242, contains claims drawn to diphenyl-imidazolyl-acetic acid morpholide or the hydrochloride salt thereof.

Buchel et al., U.S. Pat. No. 3,978,069 issued Aug. 31, 1976, which is also a division of U.S. Pat. No. 3,732,242, contains claims drawn to diphenyl-imidazolyl-acetic acid piperidine or the pharmaceutically acceptable salts thereof.

Buchel et al., U.S. Pat. No. 4,018,924 issued Apr. 19, 1977, which is a continuation-in-part of U.S. Pat. No. 3,732,242, contains claims drawn to diphenyl-imidazolyl-acetic acid piperazide, pharmaceutically acceptable salts thereof, and pharmaceutical compositions thereof.

Yih and Yu, U.S. Pat. No. 4,009,021 issued Feb. 22, 1977, assigned to the same assignee to which the present application is assigned, discloses as plant growth regulating agents compounds having the formula:

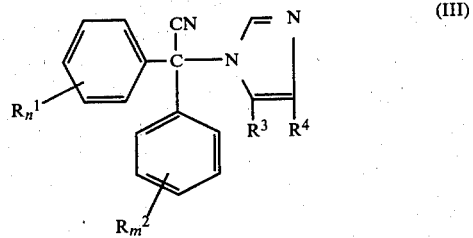

wherein:
- $R^1$ is a halogen atom, preferably a chlorine or bromine atom, an alkyl group, preferably having 1 to 4 carbon atoms, an alkoxy group, preferably having 1 to 4 carbon atoms, a trifluoromethyl group, or a nitro group,
- $R^2$ is a halogen atom, preferably a chlorine or bromine atom, an alkyl group, preferably having 1 to 4 carbon atoms, an alkoxy group, preferably having 1 to 4 carbon atoms, a trifluoromethyl group, or a nitro group,
- $R^3$ is a hydrogen atom or an alkyl group, preferably having 1 to 4 carbon atoms, most preferably a methyl group,
- $R^4$ is a hydrogen atom or an alkyl group, preferably having 1 to 4 carbon atoms, most preferably a methyl group,
- n is 0, 1, or 2, and
- m is 0, 1, or 2 and the agronomically-acceptable acid addition salts thereof. The imidazole acid addition salts include salts of the compound of formula III above with hydrochloric acid, hydrobromic acid, hydrofluoric acid, nitric acid, perchloric acid, sulfuric acid, phosphoric acid, chloracetic acid, oxalic acid, formic acid, acetic acid, maleic acid, succinic acid, benzenesulfonic acid, p-toluenesulfonic acid, tartaric acid, lactic acid, and the like.

Miller, Chan and Carley, U.S. Pat. Nos. 4,073,921 and 4,143,137, the latter being a division of the former, both being assigned to the same assignee to which the present application is assigned, disclose substituted arylcyanoalkyl and diarylcyanoalkyl imidazoles, their acid addition salts and their metal salt complexes and their use as broad spectrum protectant-eradicant fungicides.

Sury and Hoffman, *Helv. Chim. Acta.*, 37, 2133 (1954), disclose diphenyl-4-pyridylacetonitriles as intermediates for producing central nervous system stimulating agents.

British Pat. No. 1,361,816 and the corresponding Netherlands Pat. No. 7,117,312, disclose diphenyl-2-pyrazylacetonitriles having herbicidal and plant growth regulatory activity.

U.S. Pat. Nos. 3,868,244 and 3,887,708 and the corresponding French Pat. No. 1,569,940, disclose the preparation and fungicidal activity of diphenyl-5-pyrimidylacetonitriles.

U.S. Pat. No. 3,655,359 discloses diphenyl-3-pyridylacetonitriels having herbicidal activity.

SUMMARY OF THE INVENTION

It has surprisingly and unexpectedly been discovered that certain N-heterocycle-containing phenylacetonitrile derivatives are particularly and selectively effective as herbicides, especially for the control of barnyardgrass, for transplanted rice under aquatic, or flood, conditions as occurs in rice paddys.

Accordingly, the invention comprises a method for selectively regulating weed plant growth in transplanted rice fields under aquatic conditions which comprises applying to said plants in said rice fields an agronomically effective amount of a compound having the formula:

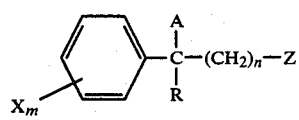

(IV)

wherein
X is selected from hydrogen, $(C_1-C_4)$ alkyl, F, Cl, Br, $NO_2$ or $SO_2C_6H_5$;
R is selected from $C_6H_5$, $C_6H_4$—X wherein X is as defined above, straight or branched chain $(C_1-C_8)$ alkyl, $(C_3-C_6)$ saturated or unsaturated cycloaliphatic groups, $C_6H_5CH_2$ or $C_6H_5S$;
n is selected from 0, 1 or 2;
m is selected from 0, 1 or 2;
A is selected from CN and C≡CH; and
Z is a N-heterocyclic group selected from:

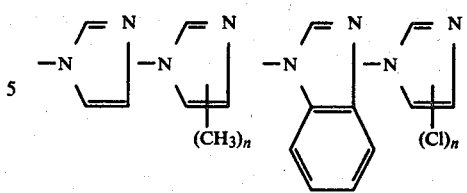

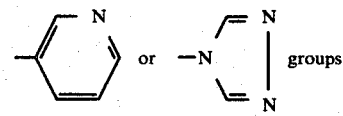

or an agronomically-acceptable acid addition salt thereof.

Preferably, the compounds useful in the method according to the invention are those having the formula IV above wherein:
X is selected from hydrogen, $(C_1-C_4)$ alkyl, F, Cl or Br;
R is selected from $C_6H_5$ or $C_6H_4$—X wherein X is H, $(C_1-C_4)$ alkyl, F, Cl or Br;
n is 0; and
Z is selected from:

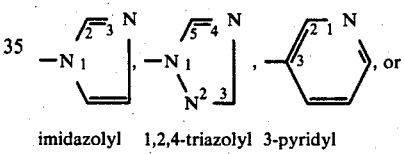

imidazolyl  1,2,4-triazolyl  3-pyridyl

 groups.

pyrazyl

Typical compounds useful in the present invention include:
α,α-diphenyl-1H-imidazolyl-1-acetonitrile,
α,α-diphenyl-1H-(4-methylimidazolyl)-1-acetonitrile,
α,α-diphenyl-1H-(5-methylimidazolyl)-1-acetonitrile,
α-(4-chlorophenyl)-α-phenyl-1H-imidazolyl-1-acetonitrile,
α-(3-methylphenyl)-α-phenyl-1H-imidazolyl-1-acetonitrile,
α,α-diphenyl-1H-(4,5-dichloroimidazolyl)-1-acetonitrile,
α-(4-methoxyphenyl)-α-phenyl-1H-imidazolyl-1-aceonitrile,
α-(3-methylphenyl)-α-(2-nitrophenyl)-1H-imidazolyl-1-acetonitrile,
α-(2-trifluoromethylphenyl)-α-phenyl-1H-imidazolyl-1-acetonitrile,
α-phenyl-α-butyl-1H-imidazolyl-1-acetonitrile,
α,α-di(2-bromophenyl)-1H-imidazolyl-1-acetonitrile,
α,α-diphenyl-1H-(1,2,4-triazolyl)-1-acetonitrile,
α,α-diphenyl-1H-(1,2,3-triazolyl)-1-acetonitrile,
α,α-diphenyl-α-(2-pyrazyl)-acetonitrile, α-(4-nitrophenyl)-α-phenyl-α-(2-pyridyl)-acetonitrile,
α,α-diphenyl-α-(3-pyridyl)-acetonitrile,
α,α-diphenyl-α-pyrazolyl-acetonitrile,
α,α-diphenyl-1H-benzimidazolyl-1-acetonitrile,
α,α-diphenyl-α-(5-pyrimidyl)-acetonitrile, and
3,3-diphenyl-3-1H -imidazolyl-propyne.

In addition to the compounds having the formula IV above, other compounds outside the scope of formula IV have been found to exhibit low, but appreciable, activity as herbicides in rice under paddy conditions. These other compounds have the general formula:

wherein R' is selected from H, Cl, Br, $N_3$, $NH_2$, $OCH_3$ or $SC_6H_5$. Because of their low herbicidal activity under rice paddy conditions, these other compounds are not considered to demonstrate practical utility according to the invention.

In another aspect, the invention comprises the compound having the formula IV above wherein:
X is selected from hydrogen, ($C_1$-$C_4$) alkyl, F, Cl, Br, $NO_2$ or $SO_2C_cH_5$;
R is selected from $C_6H_5$, $C_6H_4$—X wherein X is as defined above, straight or branched chain ($C_1$-$C_8$) alkyl, ($C_3$-$C_6$) saturated or unsaturated cycloaliphatic groups, $C_6H_5CH_2$ or $C_6H_5S$;
n is selected from 0, 1 or 2;
m is selected from 0, 1 or 2; and
Z is a triazolyl group having the empirical formula $C_2H_2N_3$.

The triazolyl group may be the 1,2,4-triazolyl group,

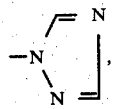

or the 1,2,3-triazolyl group,

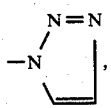

or the 1,3,4-triazolyl group

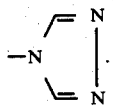

The 1,2,4-triazoyl compound is the more preferred among this group. The triazolyl compounds can be prepared by processes analogous to those processes for the preparation of the diphenyl-imidazolyl-acetonitrile compounds as disclosed by Yih and Yu, U.S. Pat. No. 4,009,021, and by Buchel et al., U.S. Pat. No. 3,732,242, except that 1,2,4-triazole or 1,2,3-triazole is substituted for imidazole in the reaction with, for example, alpha-chloro-diphenylacetonitrile. In addition to the selective herbicidal activity against weed plants in rice paddys, these triazolyl compounds also possess plant growth regulating activity as disclosed in Yih and Yu, U.S. Pat. No. 4,009,021, for the diphenyl-imidazolyl-acetonitrile compounds of the patent.

Many of the diphenyl-imidazolyl-acetonitrile compounds used according to the invention are known. These compounds and their analogs can be produced by the methods described by Yih and Yu, U.S. Pat. No. 4,009,021 and by Buchel et al., U.S. Pat. No. 3,732,242, both of which patents are mentioned above.

The preparation of the diphenyl-(4-pyridyl)- and diphenyl-(2-pyridyl)-acetonitriles used in the invention is described by Sury and Hoffman, Helv. Chem. Acta., 37, 2133 (1954) mentioned above.

The preparation of the diphenyl-(3-pyridyl)-acetonitriles is disclosed by Krumkalns and Taylor in U.S. Pat. No. 3,655,359 mentioned above.

Taylor et al., U.S. Pat. Nos. 3,868,244 and 3,887,708, mentioned above, describe the preparation of the diphenyl-(5-pyrimidyl)-acetonitriles used in the invention.

The diphenyl-(2-pyrazyl)-acetonitriles used in the invention can be produced as described in British Pat. No. 1,361,816 mentioned above.

The compounds having the formula IV are useful especially as pre-emergence, and/or post-emergence, selective herbicides for weeds which typically thrive under aquatic (flood) conditions, particularly for those weeds which thrive in transplanted rice fields (or paddys). Such weed plants include the following: barnyardgrass (*Echinochloa crus-galli*) and *Panicum crus-galli*); Monochloria (*Monochoria microiria*); spikerush (*Eleocharis acicularis*); broad leaf weeds, including American waterwort (*Elatine triandra*), Pales pimpernel (*Lindernia pyxidaria*) and Dopatrium (*Dopatrium junceum*); duckweed (*Lemna polyrhiza*); flat sedge plants; chufa; toothcup; and arrowhead.

When used according to the invention, the herbicidal compounds are applied to the plant or plant habitat in any amount which will be sufficient to effect the desired plant response without causing a significant undesirable rice phytotoxic response. Generally, the compounds will be applied to the plant or plant habitat at a rate (treating level) of about 0.1 to 10, preferably about 0.4 to 10, and most preferably about 2 to 5 pounds per acre.

The herbicidal compounds can be used either individually or in mixtures. Under some conditions, the compounds having formula IV may be used advantageously with other agricultural chemicals such as fertilizers, herbicides, fungicides, insecticides, and plant bactericides. For example, they can be used in combination with other herbicides and plant growth regulators, such as auxins, gibberellins, ethylene- releasing agents such as ethephon, pyridones, cytokinins, maleic hydrazide, succinic acid 2,2-dimethylhydrazide, choline and its salts, (2-chloroethyl) trimethylammonium chloride, triiodobenzoic acid, tributyl-2,4-dichlorobenzylphosphonium chloride, polymeric N-vinyl-2-oxazolidinones, tri(dimethylaminoethyl) phosphate and its salts, and N-di-methylamino-1,2,3,6-tetrahydrophthalamic acid and its salts.

Other herbicidal compounds with which the compounds according to formula IV may be used include 2-chloro-2',6'diethyl-N-(methoxy-methyl)acetanilide, 2-chloro-2',6'-diethyl-N-(butoxymethyl)acetanilide, S[4-chlorophenyl)methyl]diethylcarbamothioate, 2-t-butyl-4-(2,4-dichloro-5-isopropoxyphenyl-$\Delta^2$-1,3,4-oxadiazolin-5-one, 2,4-dichloro-1-(3'-methoxy-4'-nitrophenoxy)benzene, (2,4-dichlorophenoxy)acetic acid, 2-methyl-4-chlorophenoxy acetic acid, 2-(2,4,5-trichlorophenoxy)propionic acid, 7-oxabicyclo[2,2.1]heptane-2,3-dicarboxylic acid; S-ethyl hexahydro-1H-azepine-1-carbothioate, 3',4-dichloropropionanilide, and 2,4-dichlorophenyl/p-nitrophenyl ether.

A compound of the invention can be applied to the growth medium or to plants to be treated either by itself or, as is generally done, as a component in a growth regulant composition or formulation which also comprises an agronomically acceptable carrier. By "agronomically acceptable carrier" is meant any substance which can be used to dissolve, disperse, or diffuse a compound in the composition without impairing the effectiveness of the compound and which by itself has no detrimental effect on the rice paddy equipment, crops, or agronomic environment. Mixtures of the compounds of the invention may also be used in any of these formulations. The compounds of the invention can be either solid or liquid formulations or solutions. For example, the compounds can be formulated as wettable powders, emulsifiable concentrates, dusts, granular formulations, or flowable emulsion concentrates. In such formulations, the compounds are extended with a liquid or solid carrier and, when desired, suitable surfactants are incorporated.

If desired, there may be included adjuvants, such as wetting agents, spreading agents, dispersing agents, stickers, adhesives and the like, in accordance with standard agricultural practices. Examples of adjuvants which are commonly used in the art can be found in the John W. McCutcheon, Inc. publication "Detergents and Emulsifiers Annual".

The compounds used in the invention can be dissolved in any appropriate agronomically acceptable solvent. Examples of solvents which are useful in the practice of this invention include water, alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates is usually about 10% to 60% and, in flowable emulsion concentrates, this can be as high as about 75%.

Wettable powders, suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent may generally constitute about 0.5% to about 3% of the composition, and a wetting agent may generally constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain hulls, or similar material. A solution of one or more of the compounds in a volatile organic solvent can be sprayed or mixed with the granular solid and the solvent then removed by evaporation. The granular material can have any suitable size, with a preferable size range of 16 to 60 mesh. The active compound will usually comprise about 2 to 15% of the granular formulation.

The compounds of the invention can be applied as sprays by methods commonly employed, such as conventional hydraulic sprays, aerial sprays, and dusts. For low-volume applications a solution of the compound is usually used. The dilution and volume of application will usually depend upon such factors as the type of equipment employed, the method of application, and the area to be treated.

The following examples will illustrate this invention but are not intended to limit it in any way. All temperatures are in Celsius or degrees Centigrade, and all parts and percentages are by weight unless otherwise indicated.

The following abbreviations, symbols and trademarks are used in the examples hereafter:
BG=Barnyardgrass
MON=Monochoria
SPR=Spikerush
BL=Broadleaf plants
DW=Duckweed
FS=Flat sedge
AD=Average Dicot
AM=Average Monocot
Kg=kilogram
ai=active ingredient
Ha=hectare ($10^4$ m$^2$=2.471 Ac) where
 #/Ac=pounds/acre
TOK® E-25 (Rohm and Haas Company=2,4-dichlorophenyl p-nitrophenyl ether (or 2,4-dichloro-1-(4-nitrophenoxy)benzene) (U.S. Pat. No. 3,080,225)
N=Not tested A number of the more representative compounds used in the method of the invention are presented in Table I which follows:

TABLE I
HERBICIDAL COMPOUNDS

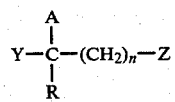

$$Y-\underset{R}{\overset{A}{C}}-(CH_2)_n-Z$$

| Compound | Y | R | A | n | Z |
|---|---|---|---|---|---|
| 1 | $C_6H_5$ | $C_6H_5$ | CN | 0 | 1H—imidazolyl |
| 2 | " | " | " | 1 | (1H—imidazolyl.$HONO_2$)methyl |
| 3 | " | " | " | 2 | 2-(1H—imidazolyl)ethyl |
| 4 | " | " | " | 0 | 1H—imidazolyl.$HONO_2$ |
| 5 | " | " | " | 0 | 1H—imidazolyl.HCl |
| 6 | " | " | " | 0 | 1H—imidazolyl.HOC(O)C(O)OH |
| 7 | " | " | " | 0 | 1H—imidazolyl.$CH_3$I |
| 8 | " | " | " | 0 | 1H—(4-methylimidazolyl): 1H—(5-methylimidazolyl) = 1:3 |
| 9 | " | " | " | 0 | 1H—benzimidazolyl |
| 10 | " | " | " | 0 | 1H—(4,5-dichloroimidazolyl) |
| 11 | " | " | " | 0 | 1,2,4-triazolyl |
| 12 | " | " | " | 0 | 1,2,3-triazolyl |
| 13 | " | " | " | 0 | pyrazolyl |
| 14 | " | " | " | 0 | 2-pyrazyl |
| 15 | " | " | " | 0 | 5-pyrimidyl |
| 16 | " | " | " | 0 | 2-pyridyl |
| 17 | " | " | " | 0 | 3-pyridyl |
| 18 | " | " | " | 0 | 4-pyridyl |
| 19 | " | 2-$ClC_6H_4$ | " | 0 | 1H—imidazolyl |
| 20 | " | 3-$ClC_6H_4$ | " | 0 | " |
| 21 | " | 4-$ClC_6H_4$ | " | 0 | " |
| 22 | " | 2-$CH_3C_6H_4$ | " | 0 | " |
| 23 | — | 3-$CH_3C_6H_4$ | " | 0 | " |
| 24 | " | 4-$CH_3C_6H_4$ | " | 0 | " |
| 25 | " | $C_6H_5S$ | " | 0 | " |
| 26 | " | $C_6H_5SO_2-C_6H_4$ | " | 0 | " |
| 27 | " | $C_4H_9$ | " | 0 | " |
| 28 | " | $C_6H_5CH_2$ | " | 0 | " |
| 29 | " | $C_6H_5$ | C≡CH | 0 | " |

Several compounds having the formula V above are presented in Table II which follows:

TABLE II $$(C_6H_5)_2-\underset{R}{\overset{CN}{C}}$$

| Compound | R |
|---|---|
| 30 | H |
| 31 | Cl |
| 32 | $NH_2$ |
| 33 | $N_3$ |
| 34 | $OCH_3$ |
| 35 | Br |
| 36 | $SC_6H_5$ |

EXAMPLE 1

Screening For Rice Paddy Weed Plant Herbicidal Activity

Herbicidal activity against barnyardgrass (BG) under aquatic conditions is determined by two "secondary" test methods. First, in a "modified beaker test", barnyardgrass is seeded (9 to 15 presoaked seeds) into 600 ml. glass beakers containing 5 cm bar sand and 5 ml flood (tap water). These seeded beakers are maintained in a heated greenhouse and the tests are run in two replicates. The treatment level of the compounds is 2# and/or 4# per acre. The tests are evaluated after 14 days.

Second, in a "petri dish method", 3½ inch diameter covered petri dishes containing filter paper are treated with the herbicidal compounds at levels of 1# and 4# per acre and then 10 ml. of tap water is added to each, followed by the introduction to each of 12 presoaked Barnyardgrass seeds. The tests are evaluated after 14 days.

The results of the "Secondary" tests, in terms of percent kill of treated plants versus untreated plants (control), are presented in Table III below on a 0–100% vs. control basis. A value of 90% or greater vs. control is considered "good".

TABLE III
HERBICIDAL ACTIVITY

| | Modified Beaker Test (Greenhouse) BG | | Petri Dish Test (Laboratory) BG | |
|---|---|---|---|---|
| Compound | 2#/Ac | 4#/Ac | 1#/Ac | 4#/Ac |
| 1 | 100 | 100 | 95 | 95 |
| 2 | 20 | 40 | 0 | 85 |
| 3 | 40 | 35 | 0 | 95 |
| 4 | 100 | 100 | 95 | 99 |
| 5 | N | N | N | N |
| 6 | 100 | 100 | 98 | 99 |
| 7 | 25 | 60 | 80 | 99 |
| 8 | 100 | 100 | 98 | 99 |
| 9 | 80 | 95 | 10 | 20 |
| 10 | N | N | N | N |
| 11 | 100 | 100 | 98 | 98 |
| 12 | 28 | 58 | 90 | 90 |
| 13 | 10 | 10 | 0 | 0 |
| 14 | 100 | 100 | 95 | 95 |
| 15 | N | N | N | N |
| 16 | N | N | N | N |
| 17 | 100 | 100 | 95 | 95 |
| 18 | 50 | 60 | 0 | 0 |
| 19 | N | 100 | N | N |
| 20 | N | 98 | N | N |
| 21 | N | 100 | N | N |
| 22 | N | 98 | N | N |

TABLE III-continued

| | HERBICIDAL ACTIVITY | | | |
|---|---|---|---|---|
| | Modified Beaker Test (Greenhouse) BG | | Petri Dish Test (Laboratory) BG | |
| Compound | 2#/Ac | 4#/Ac | 1#/Ac | 4#/Ac |
| 23 | N | 100 | N | N |
| 24 | N | 96 | N | N |
| 25 | N | 10 | N | N |
| 26 | N | 15 | N | N |
| 27 | N | 60 | N | N |
| 28 | N | 50 | N | N |
| 30 | 15 | 70 | 99 | 99 |
| 31 | 10 | 10 | 50 | 99 |
| 32 | 0 | 0 | 15 | 100 |
| 33 | 0 | 0 | 30 | 50 |
| 34 | 0 | 0 | 60 | 85 |
| 35 | 0 | 0 | 50 | 99 |
| 36 | 0 | 0 | 40 | 85 |

N = not tested

The results presented in Table III indicate that a wide variety of phenylacetonitrile derivatives having an N-heterocyclic group substituted at the α-carbon atom possess varying degrees of herbicidal activity against barnyardgrass under aquatic conditions in in vitro tests. The "modified beaker test" is considered to be more reliable in approximating rice paddy conditions than the second, "petri dish test" because the latter test appears to be particularly sensitive. The data indicate that phenylacetonitrile derivatives having the structural formula IV above may have structural variations including variation of the N-heterocyclic moiety and substituents bonded thereto, variation of the number and types of substituents on one or two of the phenyl groups bonded to the α-carbon atom, and replacement of one of the α-phenyl groups with alkyl, aralkyl and thiophenyl groups, and still exhibit herbicidal activity against barnyardgrass under aquatic (or flood) conditions. The in vitro test data indicate that compounds represented by formula IV wherein two unsubstituted phenyl groups and one of the group of unsubstituted imidazolyl, 1,2,4-triazolyl, 3-pyridyl and 2-pyrazyl groups are bonded to the α-carbon atom appear to have advantageous herbicidal activity according to the invention.

EXAMPLE 2

Preemergence Herbicidal Activity in Simulated Rice Paddy

This example illustrates the preemergence herbicidal activity in a simulated rice paddy under greenhouse conditions of one of the compounds according to the invention, Compound No. 1 (α,α-diphenyl-1H-imidazolyl-1-acetronitrile), compared with the herbicidal activity of a known preemergence herbicidal compound outside the scope of the invention, 2,4-dichloro-1-(4-nitrophenoxy)benzene, which compound is also known as 2,4-dichlorophenyl p-nitrophenyl ether. The comparative compound is known by the common name "nitrofen" and is available from the Rohm and Haas Company under the trademark TOK® E-25. Compound No. 1 and TOK® E-25 herbicide are applied as emulsified concentrates having 26% and 25% active ingredient, respectively. The variety of rice used is Nihonbare rice. Herbicidal activity is determined against barnyardgrass, Monochoria and Chara, the latter two types of plants being grouped together and labeled "others". Weed seeds are sown at several days intervals following treatment with varying levels of the herbicidal compounds and the results are evaluated ten days thereafter. The temperature is maintained at 10°–35° C. The results are presented in Table IV below.

The results demonstrate the longer residual herbicidal activity is achieved in simulated rice paddy conditions with the use of Compound No. 1 than with the known herbicidal compound.

TABLE IV

| | | SIMULATED RICE PADDY TEST | | | | | | | |
|---|---|---|---|---|---|---|---|---|---|
| Days After Treatment | | Compound No. 1 | | | | TOK E-25 | | Control (Untreated) | |
| | | 1 Kg ai/Ha | | 3 Kg ai/Ha | | 2.5 Kg ai Ha | | | |
| Sowed | Evaluated | BG | Others | BG | Others | BG | Others | BG | Others |
| 0 | 10 | — | — | — | — | — | — | + | + |
| 5 | 15 | — | — | — | — | — | — | + | + |
| 10 | 20 | — | — | — | — | ± | ± | + | + |
| 15 | 25 | — | — | — | — | + | + | + | + |
| 20 | 30 | — | — | — | — | + | + | + | + |
| 30 | 40 | ± | — | — | — | + | + | + | + |

— = No growth observed
± = Growth with some inhibition observed
+ = Normal growth (Equal growth to the untreated) observed

EXAMPLE 3

Preemergence Herbicidal Activity and Phytotoxicity of a α,αDiphenyl-1H-imidazolyl-Acetonitrile In Simulated Rice Paddy This example illustrates the preemergence herbicidal activity in a simulated rice paddy under greenhouse conditions of compounds according to the invention, exemplified by Compound No. 1, α,α-diphenyl-1H-imidazolyl-acetonitrile. Two days after transplanting, the compound is applied as an emulsified concentrate having about 26% active ingredient to Nihonbare rice plants transplanted in rice paddy soil naturally infested with weed seeds. The temperature is maintained at 12°–30° C. Weed control (against five weed plants) and phytotoxicity (rice crop injury) are evaluated 26 days following treatment.

The results, presented in Table V, demonstrate that the use of Compound No. 1 of the invention gives excellent weed control and no phytotoxicity at levels effective to give weed control.

TABLE V

| | | SIMULATED RICE PADDY TEST | | | | | |
|---|---|---|---|---|---|---|---|
| | | Crop | Weed Control* | | | | |
| Compound | Kg ai/Ha | Injury* | BG | MON | SPR | BL | DW |
| No. 1 | 0.5 | 0 | 10 | 10 | 9.5 | 9 | 10 |
| No. 1 | 1 | 0 | 10 | 10 | 9.5 | 10 | 10 |
| No. 1 | 2 | 0 | 10 | 10 | 10 | 10 | 10 |
| Untreated | — | 0 | 0 | 0 | 0 | 0 | 0 |

TABLE V-continued

SIMULATED RICE PADDY TEST

| Compound | Kg ai/Ha | Crop Injury* | BG | MON | SPR | BL | DW |
|---|---|---|---|---|---|---|---|
| (Control) | | | | | | | |

\* = crop injury, weed control: 0-10 scale (IDM index)

EXAMPLE 4

Preemergence Herbicidal Activity Against Barnyardgrass In Simulated Rice Paddy This example further illustrates the preemergence herbicidal activity in a simulated rice paddy under greenhouse conditions of several compounds according to the invention and of a known herbicide outside of the socpe of the invention applied at varying treating levels as emulsified concentrates to the transplanted Nihonbare rice. The compounds are applied just after transplanting the rice in rice paddy soil naturally infested with weed seeds. The temperature is maintained at 15°-40° C. For comparison, untreated transplanted Nihonbare rice plants are maintained under similar conditions. Weed control is evaluated 22 days following the treatment.

The results, presented in Table VI below, demonstrate that Compound No. 1 is especially effective at all levels tested. The methiodide salt of Compound No. 1, however, does not show herbicidal activity at any of the levels tested. The other compounds according to the invention demonstrate moderate to excellent herbicidal activity as the level of treatment is increased. Very slight crop injury (sheath browning) associated with the use of Compounds No. 19, 20 and 23 is observed at every treatment level. Use of the comparative compound, designated "\*\*", gives crop injury of 2, 4 and 5 according to the IDM Index system with treating levels of 0.5, 1 and 3 kg. ai/Ha, respectively.

TABLE VI

SIMULATED RICE PADDY TEST

| | % BG Control* | | | | |
|---|---|---|---|---|---|
| | Treatment (Kg ai/Ha) | | | | |
| Compound No. | 0.1 | 0.5 | 1 | 3 | 5 |
| 1 | 85 | 80 | 95 | 99 | 99 |
| 7 | 0 | 0 | 0 | 0 | 0 |
| 17 | 50 | 40 | 40 | 80 | 80 |
| 19 | 80 | 80 | 80 | 80 | 85 |
| 20 | 80 | 90 | 90 | 90 | 90 |
| 21 | 20 | 80 | 90 | 99 | 95 |
| 23 | 70 | 70 | 70 | 80 | 90 |
| \*\* | N | 70 | 75 | 80 | N |

*% BG control =

$$\left(1 - \frac{\text{number of BG plants grown in treated area}}{\text{number of BG plants grown in untreated area}}\right) \times 100$$

\*\*2,4-dichloro-1-(3'-methoxy-4'-nitrophenoxy)benzene

EXAMPLE 5

Preemergence Herbicidal Activity and Phytotoxicity In Simulated Rice Paddy

This example further illustrates the preemergence herbicidal activity and phytotoxicity in a simulated rice paddy under outdoor conditions of several compounds according to the invention and of a known herbicide outside of the scope of the invention applied at varying treating levels as emulsified concentrates to the Nihonbare rice seedlings (20 leaf age, 15-20 cm height) transplanted in rice paddy soil naturally infested with weed seeds. Three days after transplanting, the herbicidal compounds are applied dropwise onto the surface of the water in the simulated paddy and the depth of water is maintained at 3 cm. Rice phytotoxicity and weed control are evaluated after 15 days. For comparison, untreated transplanted Nihonbare rice plants are maintained under similar conditions. Weed control and phytotoxicity are evaluated 15 days after treatment.

The results, presented in Table VII below, demonstrate that compound No. 1 is especially effective at all levels tested against each of the weed plants tested. Compound No. 11, the analog of Compound No. 1 wherein a 1,2,4-triazolyl group is substituted for the 1H-imidazolyl group, is also especially effective almost to the same degree as Compound No. 1. All of the other compounds according to the invention tested show excellent herbicidal activity against monochoria and moderate to excellent effect with increasing treatment level against barnyardgrass and broad leaf weeds. As observed in other tests, the compounds containing the 2-3-chlorophenyl groups, Compounds 19 and 20, effect very slight rice phytotoxicity. Use of the comparative compound provides excellent herbicidal activity but also effects appreciable rice phytotoxicity.

TABLE VII

SIMULATED RICE PADDY TEST

| Compound No. | Kg ai/Ha | Phytotoxicity* on rice | BG | % weed control*** MON | BL** |
|---|---|---|---|---|---|
| 1 | 1 | 0 | 100 | 100 | 100 |
|   | 3 | 0 | 100 | 100 | 100 |
|   | 5 | 0 | 100 | 100 | 100 |
| 21 | 1 | 0 | 94 | 100 | 87 |
|   | 3 | 0 | 100 | 100 | 100 |
|   | 5 | 0 | 100 | 100 | 100 |
| 20 | 1 | 0 | 91 | 100 | 87 |
|   | 3 | 0.5 | 100 | 100 | 100 |
|   | 5 | 0 | 100 | 100 | 100 |
| 19 | 1 | 0 | 94 | 100 | 94 |
|   | 3 | 0 | 100 | 100 | 100 |
|   | 5 | 0.5 | 100 | 100 | 100 |
| 23 | 1 | 0 | 79 | 100 | 84 |
|   | 3 | 0 | 84 | 100 | 91 |
|   | 5 | 0 | 100 | 100 | 100 |
| 17 | 1 | 0 | 94 | 100 | 87 |
|   | 3 | 0 | 87 | 100 | 94 |
|   | 5 | 0 | 100 | 100 | 94 |
| 29 | 1 | 0 | 94 | 100 | 87 |
|   | 3 | 0 | 94 | 100 | 87 |
|   | 5 | 0 | 100 | 100 | 94 |
| 11 | 1 | 0 | 94 | 100 | 100 |
|   | 3 | 0 | 100 | 100 | 100 |
|   | 5 | 0 | 100 | 100 | 100 |
| \*\*\*\* | 1 | 3.5 | 97 | 100 | 97 |
|   | 3 | 5.0 | 100 | 100 | 100 |
| untreated | — | — | 0 | 0 | 0 |

*Phytotoxicity: On a scale of from 0 to 10, 0 means "no phytoxicity" and 10 means "all rice plants dead."
\*\*BL includes chickweed, pimpernel and toothcup weeds
\*\*\*% weed control =

$$\left(1 - \frac{\text{number of weeds grown in the treated area}}{\text{number of weeds grown in the untreated area}}\right) \times 100$$

\*\*\*\*2,4-dichloro-1-(3'-methoxy-4'-nitrophenoxy)benzene

EXAMPLE 6

This example further illustrates the rice paddy herbicidal activity and absence of rice phytotoxicity under simulated outdoor rice paddy conditions of Compound No. 1 according to the invention and of TOK E-25, a known comparative herbicide mentioned above at varying treating levels and at varying treating times. The compounds are applied as 25% emulsified concentrates 3 days before transplanting; just after transplanting, and 3 days after transplanting Nihonbare rice plants in rice paddy soil naturally infested with weed seeds. The depth of water is maintained at about 3 cm to 5 cm. Rice phytotoxicity and weed control (that is, broad leaf weed control) are evaluated after two weeks and reported as described in Example 5 above.

The results, presented in Table VIII below, demonstrate that Compound No. 1 according to the invention is especially herbicidally effective against broad leaf weeds at treating levels of 0.5–3 kg/Ha when applied before or at the time of transplanting rice plants. This compound is only slightly less effective when applied after transplanting. Use of TOK E-25 provides good to excellent herbicidal effectiveness but suffers the disadvantage of effecting appreciable rice phytotoxicity.

TABLE VIII

SIMULATED RICE PADDY TEST

| Compound No. | Kg ai/Ha | *Treating time | Rice Phytotoxicity 1 week | 2 weeks | % Weed Control after 2 weeks | | |
|---|---|---|---|---|---|---|---|
| 1 | 0.5 | −3 | 0 | 0 | 100 | 100 | 100 |
|  |  | 0 | 0 | 0 | 100 | 100 | 100 |
|  |  | +3 | 0 | 0 | 95 | 100 | 95 |
|  |  | −3 | 0 | 0 | 100 | 100 | 100 |
|  |  | 0 | 0 | 0 | 100 | 100 | 100 |
|  |  | +3 | 0 | 0 | 100 | 100 | 100 |
| 1 | 3 | −3 | 0 | 0 | 100 | 100 | 100 |
|  |  | 0 | 0 | 0 | 100 | 100 | 100 |
|  |  | +3 | 0 | 0 | 100 | 100 | 100 |
| TOK E-25 | 2.1 | −3 | 1.0 | 1.5 | 95 | 100 | 90 |
|  |  | 0 | 1.5 | 2.0 | 100 | 100 | 90 |
|  |  | +3 | 1.5 | 2.0 | 100 | 100 | 90 |
| Untreated | — | — | 0 | 0 | 0 | 0 | 0 |

*Treating time:
−3 = 3 days before transplanting
0 = transplanting
+3 = 3 days after transplanting

EXAMPLE 7

Preparation of α,α-Diphenyl-1H-1,2,4-Triazolyl-1-Acetonitrile

A mixture of 775 g. (4.0 m.) of diphenylacetonitrile and 835 g. (4.4 m.) of phosphorous pentachloride is heated at 110° C. overnight. The reaction mixture is poured into water and extracted with ether. The combined ether extracts are washed with 10% hydrochloric acid saturated aqueous sodium bicarbonate solution and dried over magnesium sulfate. The solvent is evaporated to give 896.5 g. of crude α-chlorodiphenylacetonitrile.

A mixture containing 22.8 g. of α-chlorodiphenylacetonitrile and 20.8 g. of 1,2,4-triazole is heated at 110° C. with stirring overnight. The reaction mixture is poured into an ether/ammonium hydroxide mixture and shaken well either phase is washed with dilute ammonium hydroxide, saturated aqueous sodium chloride solution and dried over magnesium sulfate. The solvent is evaporated to give 21.6 g. of a light orange solid, mp. 119.5°–121.5° C.

Anal. Calcd. for $C_{16}H_{12}N_4$: C,73.82; H,4.66; N,21.53. Found: C,74.29; H,4.77; N,21.52.

EXAMPLE 8

Preparation of α,α-Diphenyl-1H-(1,2,3-Triazolyl)-1-Acetonitrile

To 22.7 g. (0.1 mole) of α-chlorodiphenylacetonitrile under nitrogen at room temperature was added 14.1 g. (0.1 mole) of 2-trimethylsilyl-1,2,3-triazole and the mixture heated at 130° C. overnight, then poured into a mixture of ether and ammonium hydroxide. The ether phase was washed with water and ammonium hydroxide, treated with charcoal, and filtered through activated silica gel. Removal of the solvent gave 20.81 g. of red-black oil. Chromatography on activated silica gel and elution with toluene yielded 6.9 g. of black oil which crystallized overnight. Recrystallization from hexane gave 2.65 g. of the title compound as white needles, m.p. 85°–86.5° C.

What is claimed is:

1. A method for selectively controlling preemergence weed plant growth in transplanted rice fields under aquatic conditions which comprises applying to said plants or plant habitat in said rice fields before, at the time of, or after transplanting the rice plants an inhibiting amount of a compound having the formula:

[chemical structure]

wherein
X is selected from hydrogen, $(C_1-C_4)$alkyl, F, Cl, Br, $NO_2$ or $SO_2C_6H_5$;
R is selected from $C_6H_5$, $C_6H_4$—X wherein X is as defined above, straight or branched chain $(C_1-C_8)$ alkyl, $(C_3-C_6)$ saturated or unsaturated cycloaliphatic groups, $C_6H_5CH_2$— or $C_6H_5S$—;
n is selected from 0, 1 or 2;
m is selected from 0, 1 or 2;
A is selected from CN and C≡CH; and
Z is a N-heterocyclic group selected from:

[chemical structures of N-heterocyclic groups]

or an agronomically acceptable acid addition salt thereof.

2. The method of claim 1 wherein

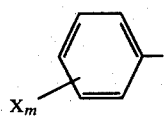

is $C_6H_5$, and R is selected from $C_6H_5$, $C_6H_4-X$ wherein X is $CH_3$, Cl or $C_6H_5SO_2$, $C_4H_9$, $C_6H_5CH_2$ or $C_6H_5S$.

3. The method of claim 2 wherein
R is $C_6H_5$;
n is 0; and
Z is selected from:

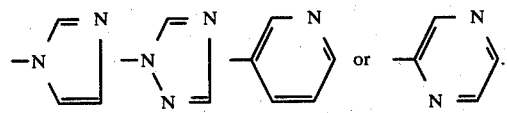

4. The method of claim 1 wherein the compound is applied to the weed plant or the locus of the weed plant at the rate of from about 0.1 to 10 pounds per acre.

5. The method of claim 1 wherein the weed plant is one or more of the group consisting of barnyardgrass, Monochoria, spikerush, flat sedge, broad leaf weeds and duckweed.

6. The method of claim 3 wherein said compound is

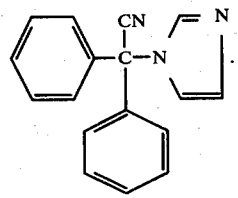

7. The method of claim 3 wherein said compound is

8. The method of claim 3 wherein said compound is

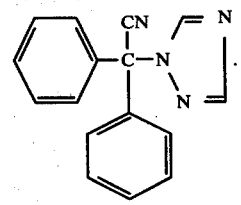

9. The method of claim 3 wherein said compound is

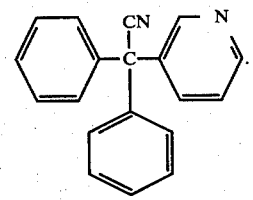

10. The method of claim 3 wherein said compound is

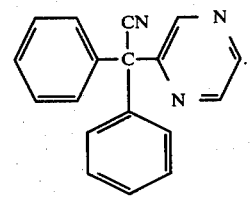

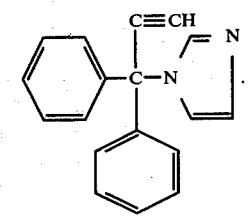

* * * * *